United States Patent [19]

Schuurman

[11] Patent Number: Plant 5,332

[45] Date of Patent: Nov. 13, 1984

[54] ROSE PLANT

[75] Inventor: Frank B. Schuurman, Auckland, New Zealand

[73] Assignee: DeVor Nurseries, Inc., Pleasanton, Calif.

[21] Appl. No.: 469,650

[22] Filed: Feb. 25, 1983

[51] Int. Cl.[3] ..... A01H 5/00

[52] U.S. Cl. ..... Plt./18

[58] Field of Search ..... Plt./18

*Primary Examiner*—Robert E. Bagwill

*Attorney, Agent, or Firm*—Vincent G. Gioia

[57] ABSTRACT

A new grandiflora rose variety of French Rose coloring which is a sport of the rose known as "Meihelvet" (commercially known as "Sonia" and "Sweet Promise") which is the subject of U.S. Plant Pat. No. 3,095, issued Apr. 4, 1972.

1 Drawing Figure

1

The present invention relates to a new and distinct variety of rose plant of the grandiflora rose class, which was discovered by me in Auckland, New Zealand. The denomination of the new variety is Suncredel.

Among the novel characteristics possessed by this new variety which distinguish it from the cultivar from which it sported, and all other varieties of which I am aware, are its bud and flower coloring and petalage while retaining the flower form, flowering characteristics, foliage and habit of growth of the host cultivar known as Meihelvet. Thus, except for petalage and coloring, the new variety is essentially the same as the aforementioned rose cultivar "Meihelvet" which is fully described in U.S. Plant Pat. No. 3,095, to which reference may be made for further horticultural description. Asexual reproduction by budding of the new variety as performed in Auckland, New Zealand, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the unique characteristicss of my new variety, with color terminology in accordance with The Royal Horticultural Society Colour Chart (R.H.S.C.C.). The terminology used in color description herein refers to plate numbers in the aforementioned color chart, e.g., "49D" is plate 49D of The Royal Horticultural Society Colour Chart.

2

Mutation: Of the rose known as "Meihelvet" ("Sonia", "Sweet Promise")
U.S. Plant Pat. No. 3,095.
Class: Grandiflora.

The following observations are made of specimens grown in Auckland, New Zealand during the month of November.

My new variety has long, pointed flower buds initially displaying an apricot coloring 24D, lightly flushed with 29C, as the sepals divide and before the sepals fall. After the sepals fall and petals become more visible, Venetian pink 49C coloring of the petals' undersurfaces, edged slightly with 24D, is seen. Upon opening further, to about the $\frac{1}{3}$–$\frac{1}{2}$ open stage, the predominant coloring is French Rose 49D (top and undersurface of petals). However, there is a sense of apricot coloring in the area where the petals are attached. The apricot coloring, 24D, is more visible in the open bloom where it is enhanced by yellow coloring of the stamens and stigma. Upon aging, the French Rose coloring lightens slightly while retaining the delicate color quality. The petalage of my new variety is generally 35–40 petals.

I claim:

1. A new and distinct variety of rose plant of the grandiflora rose class, substantially as shown and described, which is a color sport of the rose identified as "Meihelvet" in U.S. Plant Pat. No. 3,095 and is characterized particularly by French Rose colored flowers retaining color well and lightening only slightly upon aging.

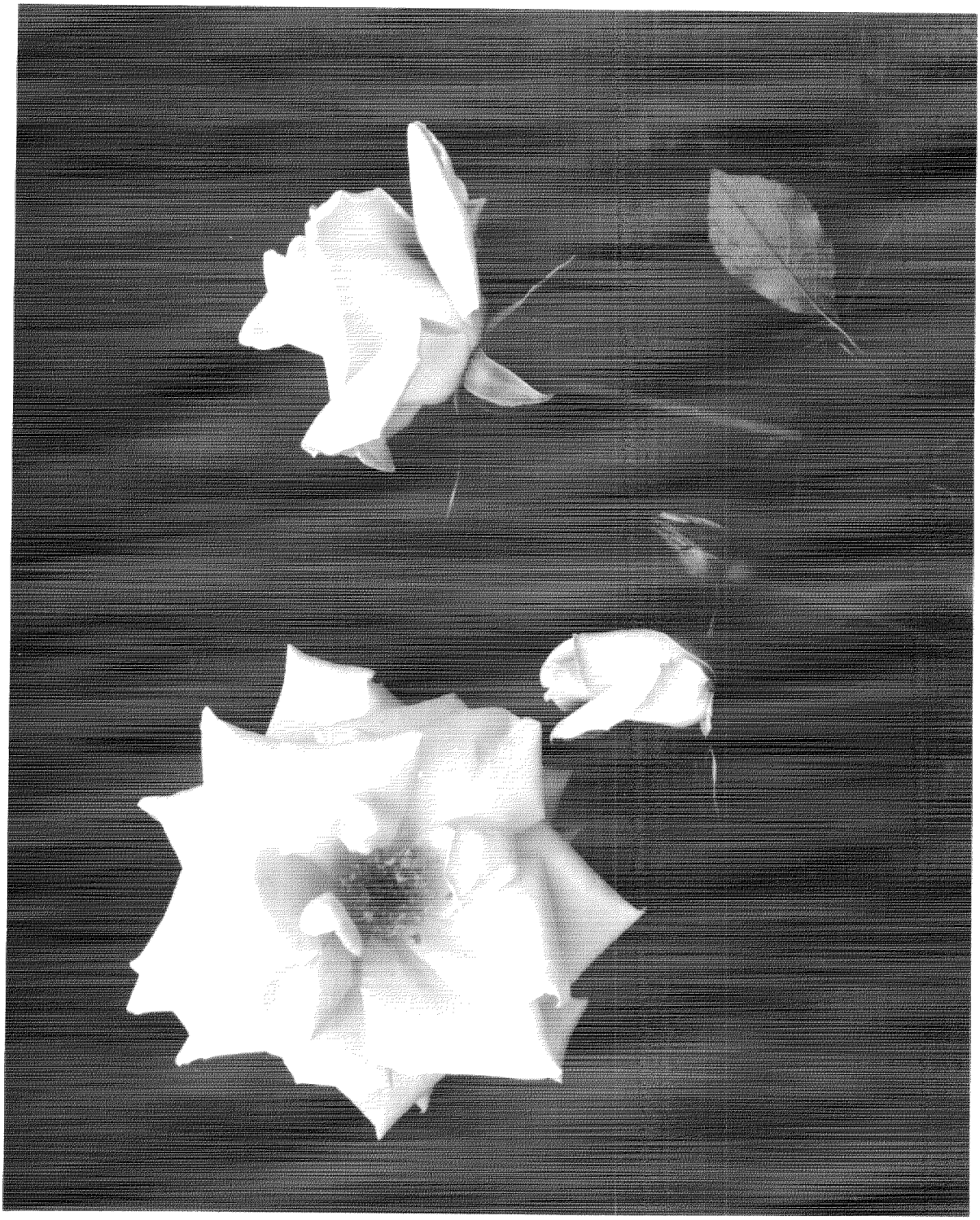

* * * * *